(12) United States Patent
Caban et al.

(10) Patent No.: US 11,524,159 B2
(45) Date of Patent: Dec. 13, 2022

(54) CONTROL SYSTEM FOR CLOSED-LOOP NEUROMODULATION

(71) Applicant: ONWARD MEDICAL N.V., Eindhoven (NL)

(72) Inventors: Miroslav Caban, Eindhoven (NL); Niek Borgers, Eindhoven (NL); Urs Keller, Eindhoven (NL); Joachim von Zitzewitz, Eindhoven (NL); Jurriaan Bakker, Eindhoven (NL); Vincent Delattre, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 311 days.

(21) Appl. No.: 16/682,873

(22) Filed: Nov. 13, 2019

(65) Prior Publication Data

US 2020/0147383 A1 May 14, 2020

(30) Foreign Application Priority Data

Nov. 13, 2018 (EP) .................................... 18205811

(51) Int. Cl.
*A61N 1/36* (2006.01)
*A61N 1/04* (2006.01)

(52) U.S. Cl.
CPC ..... *A61N 1/36031* (2017.08); *A61N 1/36003* (2013.01)

(58) Field of Classification Search
CPC .............. A61N 1/36003; A61N 1/0452; A61N 1/0484; A61N 1/36034; A61N 1/36146; A61B 5/11; A61B 5/1124
See application file for complete search history.

(56) References Cited

U.S. PATENT DOCUMENTS 7,742,037 B2   6/2010  Sako et al.
8,326,569 B2  12/2012  Lee et al.
(Continued)

FOREIGN PATENT DOCUMENTS

EP   2868343 A1   5/2015
EP   3184145 A1   6/2017
(Continued)

OTHER PUBLICATIONS

Bizzi, E. et al., "Modular Organization of Motor Behavior," Trends in Neurosciences, vol. 18, No. 10, Oct. 1995, 8 pages.
(Continued)

*Primary Examiner* — Jon Eric C Morales
(74) *Attorney, Agent, or Firm* — Finnegan, Henderson, Farabow, Garrett & Dunner LLP

(57) ABSTRACT

A control system for a movement reconstruction and/or restoration system for a patient, comprising
  a sampling module configured and arranged to sample signals describing directly and/or indirectly motion at a sampling rate of at least 50 Hz;
  at least one stimulation system configured and arranged to provide stimulation for movement reconstruction and/or restoration to the patient;
  a prediction module configured and arranged to provide a prediction of at least a next movement, especially movement stage and/or sequence, to reduce latency and to synchronize stimulation to the movement phase,
  wherein the control system further comprises at least one controller, the controller being configured and arranged to provide stimulation control signals to the stimulation system on the basis of the information obtained by the sampling module and the prediction provided by the prediction module.

19 Claims, 9 Drawing Sheets

(56) References Cited

U.S. PATENT DOCUMENTS

| | | |
|---|---|---|
| 9,314,190 B1 | 4/2016 | Giuffrida et al. |
| 2014/0277271 A1* | 9/2014 | Chan .................. A61N 1/36003 607/48 |
| 2016/0175586 A1 | 6/2016 | Edgerton et al. |
| 2017/0157396 A1* | 6/2017 | Dixon .................. A61N 1/36146 |

FOREIGN PATENT DOCUMENTS

| | | |
|---|---|---|
| WO | 0234331 A2 | 5/2002 |
| WO | 2005002663 A2 | 1/2005 |
| WO | WO 2012/003451 A2 | 1/2012 |
| WO | 2012080964 A1 | 6/2012 |
| WO | 2014205356 A2 | 12/2014 |
| WO | 2016110804 A1 | 7/2016 |
| WO | 2017058913 A1 | 4/2017 |
| WO | 2017062508 A1 | 4/2017 |

OTHER PUBLICATIONS

Merrill, D. et al., "Electrical stimulation of excitable tissue: design of efficacious and safe protocols," Journal of Neuroscience Methods, vol. 141, No. 2, Feb. 15, 2005, 28 pages.

Courtine, G. et al., "Transformation of nonfunctional spinal circuits into functional states after the loss of brain input," Nature Neuroscience, vol. 12, No. 10, Oct. 2009, Available Online Sep. 20, 2009, 20 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.

Van Den Brand, R. et al., "Restoring Voluntary Control of Locomotion after Paralyzing Spinal Cord Injury," Science, vol. 336, No. 6085, Jun. 1, 2012, 5 pages.

Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.

Levine, A. et al., "Identification of cellular node for motor control pathways," Nature Neuroscience, vol. 17, No. 4, Apr. 2014, Available Online Mar. 9, 2014, 22 pages.

Angeli, C. et al., "Altering spinal cord excitability enables voluntary movements after chronic complete paralysis in humans," Brain: A Journal of Neurology, vol. 137, No. 5, May 2014, Available Online Apr. 8, 2014, 16 pages.

Danner, S. et al., "Human spinal locomotor control is based on flexibly organized burst generators," Brain: A Journal of Neurology, vol. 138, No. 3, Mar. 2015, Available Online Jan. 12, 2015, 12 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Capogrosso, M. et al., "A Brain-Spinal Interface Alleviating Gait Deficits after Spinal Cord Injury in Primates," Nature, vol. 539, No. 7628, Nov. 10, 2016, 39 pages.

Extended European Search Report in counterpart European Patent Application No. 18205811.5 dated Dec. 21, 2018, 6 pages.

* cited by examiner

| Fiber type | Diameter (μm) | Function |
|---|---|---|
| Ia (A-α) | 12-20 | Proprioception from muscle spindles |
| Ib (A-α) | 12-20 | Proprioception from Golgi tendon organs |
| II (A-β) | 5-12 | Fine touch, (2-point discrimination & vibration) |
| III (A-δ) | 2-5 | Light touch, fast pain & temperature |
| IV (C) | 0.5-1 | Slow pain & temperature |

Fig. 3

| # | FMB | Agonist | Antagonist |
|---|---|---|---|
| 1 | Right Ankle Extension | Right medial gastrocnemius, soleus | Right tibialis anterior |
| 2 | Right Ankle Flexion | Right tibialis anterior | Right medial gastrocnemius, soleus |
| 3 | Right Knee Extension | Right rectus femoris, vastus lateralis | Right iliopsoas, semitendinosus |
| 4 | Right Hip Extension | Right gluteus maximus, semitendinosus | Right iliopsoas, rectus femoris |
| 5 | Right Hip Flexion | Right iliopsoas, rectus femoris | Right gluteus maximus, semitendinosus |
| 6 | Right Trunk Stability | Right paraspinal muscles | |
| 7 | Left Ankle Extension | Left medial gastrocnemius, soleus | Left tibialis anterior |
| 8 | Left Ankle Flexion | Left tibialis anterior | Left medial gastrocnemius, soleus |
| 9 | Left Knee Extension | Left rectus femoris, vastus lateralis | Left iliopsoas, semitendinosus |
| 10 | Left Hip Extension | Left gluteus maximus, semitendinosus | Left iliopsoas, rectus femoris |
| 11 | Left Hip Flexion | Left iliopsoas, rectus femoris | Left gluteus maximus, semitendinosus |
| 12 | Left Trunk Stability | Left paraspinal muscles | |

Fig. 5

FMB/CMB used in Task 1

| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

FMB/CMB used in Task 2

| RIGHT ANKLE EXTENSION | LEFT ANKLE EXTENSION |
| RIGHT ANKLE FLEXION | LEFT ANKLE FLEXION |
| RIGHT KNEE EXTENSION | LEFT KNEE EXTENSION |
| RIGHT HIP EXTENSION | LEFT HIP EXTENSION |
| RIGHT HIP FLEXION | LEFT HIP FLEXION |
| RIGHT TRUNK STABILITY | LEFT TRUNK STABILITY |
| CUSTOM FUNCTIONAL BLOCK 1 | CUSTOM FUNCTIONAL BLOCK N |

Fig. 6

CONTROL SYSTEM FOR CLOSED-LOOP NEUROMODULATION

CROSS-REFERENCE TO RELATED APPLICATIONS

The present application claims priority to European Patent Application No. 18205811.5 and filed on Nov. 13, 2018. The entire contents of the above-listed application is hereby incorporated by reference for all purposes.

TECHNICAL FIELD

The present invention relates to a system for controlling a movement reconstruction and/or restoration system for a patient, e.g. in the field of improving recovery after neurological disorders like spinal cord injury (SCI), for example after trauma.

BACKGROUND AND SUMMARY

Decades of research in physiology have demonstrated that the mammalian spinal cord embeds sensorimotor circuits that produce movement primitives (cf. Bizzi E. et al., *Modular organization of motor behavior in the frog's spinal cord. Trends in neurosciences* 18, 442-446 (1995); Levine A J. et al., *Identification of a cellular node for motor control pathways. Nature neuroscience* 17, 586-593 (2014)). These circuits process sensory information arising from the moving limbs and descending inputs originating from various brain regions in order to produce adaptive motor behaviors.

A spinal cord injury interrupts the communication between the spinal cord and supraspinal centers, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf. van den Brand R. et al., *Restoring Voluntary Control of Locomotion after Paralyzing Spinal Cord Injury. Science* 336, 1182-1185 (2012); Angeli C A. et al., *Altering spinal cord excitability enables voluntary movements after chronic complete paralysis in humans. Brain: a journal of neurology* 137, 1394-1409 (2014); Harkema S. et al., *Effect of epidural stimulation of the lumbosacral spinal cord on voluntary movement, standing, and assisted stepping after motor complete paraplegia: a case study. The Lancet* 377, 1938-1947 (2011); Danner S M et al., *Human spinal locomotor control is based on flexibly organized burst generators. Brain: a journal of neurology* 138, 577-588 (2015); Courtine G. et al., *Transformation of nonfunctional spinal circuits into functional states after the loss of brain input. Nature neuroscience* 12, 1333-1342, (2009); Capogrosso M et al., *A brain-spine interface alleviating gait deficits after spinal cord injury in primates. Nature* 539, 284-288, (2016)).

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, the system comprising means for applying to a subject neuromodulation with adjustable stimulation parameters, said means being operatively connected with a real-time monitoring component comprising sensors continuously acquiring feedback signals from said subject. The feedback signals provide features of motion of a subject, wherein the real-time monitoring component is operatively connected with a signal processing device receiving feedback signals and operating real-time automatic control algorithms. This known system improves consistency of walking in a subject with a neuromotor impairment. A Real Time Automatic Control Algorithm is used, comprising a feedforward component employing a single input-single output model (SISO), or a multiple input-single output (MISO) model. Reference is also made to Wenger N. et al., *Closed-loop neuromodulation of spinal sensorimotor circuits controls refined locomotion after complete spinal cord injury, Science Translational Medicine*, 6, 255 (2014).

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

EP 3 184 145 A1 discloses systems for selective spatiotemporal electrical neurostimulation of the spinal cord. A signal processing device receiving signals from a subject and operating signal-processing algorithms to elaborate stimulation parameter settings is operatively connected with an Implantable Pulse Generator (IPG) receiving stimulation parameter settings from said signal processing device and able to simultaneously deliver independent current or voltage pulses to one or more multiple electrode arrays. The electrode arrays are operatively connected with one or more multi-electrode arrays suitable to cover at least a portion of the spinal cord of said subject for applying a selective spatiotemporal stimulation of the spinal circuits and/or dorsal roots, wherein the IPG is operatively connected with one or more multi-electrode arrays to provide a multipolar stimulation. Such system advantageously allows achieving effective control of locomotor functions in a subject in need thereof by stimulating the spinal cord, in particular the dorsal roots, with spatiotemporal selectivity.

EP 2 652 676 A1 relates to a gesture control for monitoring vital body signs and reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heartbeat, walking, etc. Similar solutions for tapping detection of a user are known from U.S. Pat. Nos. 8,326,569 and 7,742,037.

WO 2017/062508 A1 discloses a system for controlling a therapeutic device and/or environmental parameters including one or more body worn sensor devices that detect and report one or more physical, physiological, or biological parameters of a person in an environment. The sensor devices can communicate sensor data indicative of the one or more physical, physiological, or biological parameters of a person to an external hub that processes the data and communicates with the therapeutic device to provide a therapy (e.g., neuromodulation, neurostimulation, or drug delivery) as a function of the sensor data. In some embodiments, the therapeutic device can be implanted in the person. In some embodiments, the therapeutic device can be in contact with the skin of the person. The sensor devices can also communicate to the hub that communicates with one or more devices to change the environment as a function of the sensor data.

WO2016/110804 A1 describes a number of inventions comprising one or more wearable devices (i.e. attached or applied to limbs, body, head or other body extremities but also applicable to implanted or physiologically attachable systems). These systems have a means of enabling diagnostic or prognostic monitoring applicable to monitoring relevant parameters and corresponding analysis determination and characterization applicable to the onset or detection of events or health conditions of interest. One application relates to sleep monitoring and associate EEG sensors.

WO2017/058913 A1 relates to systems and methods to analyze gait, balance or posture information extracted from data collected by one or more wearable and connected sensor devices with sensors embedded there within. The embedded sensors include a three-axis accelerometer, a three-axis gyroscope and an array of pressure sensors. Sensor data detected by the sensors can be received by a mobile computing device, which can analyze the sensor data to identify a pattern related to gait, balance or posture within the sensor data; and apply a statistical/machine learning-based classification to the pattern related to gait, balance or posture to assign a clinical parameter to the pattern characterizing a risk of a slip, trip and fall event.

WO2014/205356 A2 describes a sensor system and process for measuring electromagnetic activity of a brain. The system and process employ a sensor assembly having a plurality of electrodes arranged in a closely spaced arrangement and a processor to determine a weighted average of the signals indicative of an electric field generated by electromagnetic activity of the brain. The system provides a medical body area network of a subject including one or more of the sensor assemblies and one or more additional sensors, which may be within a smartphone or other wearable device.

WO2005/002663 A2 discloses a method for generating an electrical signal for use in biomedical applications, including two timing-interval generators, each optionally driving a multistep sequencer; analog, digital or hybrid means for combining the resulting timed signals into a complex electrical signal; optional filtering means for blocking direct current, removing selected frequency components from the resulting signal, and/or providing voltage stepup if needed; and conductive means for coupling the resulting signal to a human or animal body, food, beverage or other liquid; cell or tissue culture, or pharmaceutical material, in order to relieve pain, stimulate healing or growth, enhance the production of specific biochemicals, or devitalize selected types of organisms.

According to the state of the art, smooth movements comparable to healthy subjects still cannot be achieved by the subject. There is no available system which overcomes the drawbacks of the prior art. In particular, there is the need of a system stimulating the patient not as a robot. A good roll of the foot and no parasite movements are necessary during walking and smooth movements are necessary during any other movement including but not limited to cycling and/or swimming and/or rowing and/or stepping and/or sitting down and/or standing up. Thus, the goal of applying stimulation is not to control the patient as a robot, but to support the patient during training and daily life activities, including but not limited to walking and/or cycling and/or swimming and/or rowing and/or stepping and/or sitting down and/or standing up and/or or any other movement. Hence, a control system should be able to determine movement events, e.g. gait events, with criteria that are common to all kinds of healthy or pathological movement, e.g. gait, and should support the patient's own natural control loop composed of the brain, nervous system, and sensory organs. Thus, a control system should enable real-time synchronization of stimulation and motion.

It is an object of the present invention to improve a neurostimulation system, e.g. in the field of improving recovery after neurological disorders like spinal cord injury (SCI), for example after trauma, especially in adding a control system for a movement reconstruction and/or restoration system for a patient.

This object is solved according to the present invention by a control system for a movement reconstruction and/or restoration system for a patient, with the features of claim 1. Accordingly, this object is solved by a control system for a movement reconstruction and/or restoration system for a patient, comprising a sampling module configured and arranged to sample signals describing directly and/or indirectly motion at a sampling rate of at least 50 Hz at least one stimulation system configured and arranged to provide stimulation for movement reconstruction and/or restoration to the patient;

a prediction module configured and arranged to provide a prediction of at least a next movement, especially movement stage and/or sequence, to reduce latency and to synchronize stimulation to the movement phase, wherein the control system further comprises at least one controller, the controller being configured and arranged to provide stimulation control signals to the stimulation system on the basis of the information obtained by the sampling module and the prediction provided by the prediction module.

The invention is based on the basic idea that in the context of neuromodulation, especially neurostimulation, the electrical stimulation parameters defining the stimulation in a movement reconstruction and/or restoration system for a patient can be controlled with said system, wherein at least one controller provides stimulation control signals to the stimulation system on the basis of the information obtained by the sampling module and the prediction provided by the prediction module to reduce latency and to synchronize stimulation to the movement. The use of a general concept including a sampling module, a stimulation system, a prediction model, and at least one controller for a movement reconstruction and/or restoration system for a patient being equipped with the movement reconstruction and/or restoration system enables triggering neurostimulation based on sensor input data. The control system may interfere with the natural feedback loop of the patient to enable smooth motion, e.g. a regular gait cycle comparable to a healthy subject.

The system can be used for treatment related but not limited to restoring and/or training of the movements of the patient. These movements may include but are not limited to walking, running, stepping, swimming cycling, rowing, standing up and/or sitting down.

To estimate the movement, e.g. gait phase, the body kinematics need to be determined. For walking, in particular lower body kinematics need to be determined.

The sampling module may be linked to or may comprise one or more sensors.

To do so, sensors measure the acceleration and orientation of the limbs and/or part of the limbs at a sufficiently high rate and sufficiently low latency, such that the measured acceleration and orientation known to the control system closely match the true acceleration and orientation of the limbs and/or part of the limbs.

The optimal sample rate may be calculated following the Nyquist-Shannon sampling theorem. In the field of digital signal processing, the sampling theorem is a fundamental bridge between continuous-time signals (often called "analog signals") and discrete-time signals (often called "digital signals"). It establishes a sufficient condition for a sample rate that permits a discrete sequence of samples to capture all the information from a continuous-time signal of finite bandwidth.

In particular, the Nyquist-Shannon sampling theorem states that, under suitable assumptions, in an analog-to-digital conversion the minimum sampling frequency necessary to avoid ambiguity and loss of information (e.g., aliasing) in the reconstruction of the original analog signal is equal to twice its maximum frequency.

Alternatively, the optimal sampling rate may be at least 5 to 10 times the highest significant frequency present in the analog signal. Sensors may collect motion data, based on which the motion is determined in real-time. We define real-time as an end-to-end latency that is less than 100 ms, preferably less than 50 ms. This may be done directly by attaching sensors to the body and/or parts of the body of a subject, e.g. the lower body only, and/or a training entity, or indirectly by measuring muscle activation or by measuring the interaction between the body and/or parts of the body of a subject and their surroundings. So, for walking, the sensor may enable to determine gait phase, cadence and gait events (pre-swing, swing, loading response and stance; and/or the events toe-off, midswing, heel strike, foot flat, midstance, heel-off) with criteria that are common to all kind of healthy or pathological gait. Similarly, for cycling, the sensor may enable to determine pedal phase.

The sensors may be or may comprise at least one of an inertial measurement unit (IMU), an optical sensor, a camera, a piezo element, a velocity sensor, an accelerometer, a magnetic sensor, a torque sensor, a pressure sensor, a displacement sensor, a contact sensor, an EMG sensor, a goniometer, a hall sensor and/or a gyroscope and/or motion tracking video camera, or infra-red camera.

Said IMU may measure and report 3D accelerations, 3D angular velocities and 3D orientation using a combination of one or more of an accelerometer, one or more of gyroscopes, and optionally one or more of a magnetometer. Optionally, a temperature sensor may also be included to compensate for the effect of temperature on sensor readings. By integrating the angular velocity assessed by said one or more gyroscope and fusing with data from said one or more accelerometers, it may be possible to get a precise measurement of the angle of the foot. This angle may have a regular and characteristic pattern for healthy subject but not for injured patient. Based on these measurements the orientation of the IMU with respect to the fixed world can be estimated accurately, using standard sensor fusion algorithms.

The sensor may be configured and arranged to be inserted and/or integrated into and/or onto an exoskeleton, tights, a belt, straps, a stretching band, a knee sock, a sock and/or a shoe of the patient.

Said motion sensor may be intended to be placed on the foot to get to most information possible about the gait. The motion sensor may be configured and arranged to be inserted and/or arranged in the shoe and/or into the sole and/or into the insole of a shoe of the patient.

In particular, said sensor may be placed either on top of the instep at the back of the heel, and/or below the heel of the foot (e.g. in a pocket in the sole of the shoe and/or as an inlay sole), and/or on the sides of the foot, and/or on top of the toes. In this way, real-time and non-real-time reconstruction of foot trajectories may be done up to a few centimeters accuracy. Here, real-time is defined as an end-to-end latency that is less than 100 ms, preferably less than 50 ms.

In particular, said sensors may be placed at different positions in the shoe and/or into the shoe sole and/or into the shoe insole. One shoe and/or one shoe sole and/or one shoe insole may be equipped with one or more sensors. Said sensors may be placed in the heel area and/or the metatarsal area and/or the toe area.

The feet may be chosen as these are the lower body segments that experience the largest accelerations and angular velocities. In particular, two or more sensors placed on one foot may provide a precise description of the cadence, pre-swing, swing, loading response and stance (and/or toe-off, midswing, heel strike, foot flat and midstance) can be identified. The same events and parameters can be identified for the other foot of the patient. By combining signals of both feet, together with the gait phase and cadence of the stimulation input, a reliable gait phase and cadence estimate can be provided.

In particular, pressure sensors or contact sensors may be of interest for motion, e.g. gait, tracking, and for other applications. In particular, two or more pressure sensors placed on one foot may provide a precise map of the foot force. In particular, two or more pressure sensors placed on one insole and/or sole may provide a precise description of the cadence; pre-swing, swing, loading response and stance (and/or the events toe-off, midswing, heel strike, foot flat, midstance, heel-off) can be identified. The same events and parameters can be identified for the other foot of the patient. By combining signals of both feet, together with the gait phase and cadence of the stimulation input, a reliable gait phase and cadence estimate can be provided. For example, when a sensor is placed at the heel area, lifting the foot will result in a change of pressure or change of acceleration, speed or the like. Also, when thinking of a piezo element in a sock or other wearable, this movement will change the applied tension on the piezo element and the wearable. Similar functionality can be used at different positions or parts of the body.

Said sensors may be lightweight and wearable, thus the sensors may not hamper the movement of the patient.

Two or more sensors may form a sensor network.

Neural stimulation may be achieved by electrical stimulation, optogenetics (optical neural stimulation), chemical stimulation (implantable drug pump), ultrasound stimulation, magnetic field stimulation, mechanical stimulation, etc.

Known electrical stimulation systems use either Central Nervous System (CNS) stimulation, especially Epidural Electrical Stimulation (EES), or Peripheral Nervous System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso, M, et al., *A Computational Model for Epidural Electrical Stimulation of Spinal Sensorimotor Circuits, Journal of Neuroscience,* 33 (49), 19326-19340 (2013); Courtine G., et al., *Transformation of nonfunctional spinal circuits into functional states after the loss of brain input, Nat Neurosci.* 12(10), 1333-1342 (2009); Moraud E M., et al, *Mechanisms Underlying the Neuromodulation of Spinal Circuits for Correcting Gait and Balance Deficits after Spinal Cord Injury, Neuron,* 89(4), 814-828 (2016)). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies.

Peripheral Nervous System (PNS) Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set of reflexes (practically limited to the withdrawal reflex) or through transcutaneous stimulation of the peripheral nerves. The resulting muscle fatigue renders FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

It is possible to provide neuromodulation and/or neurostimulation with the system to the CNS with a CNS stimulation system and/or to the PNS with a PNS stimulation system. Note that the CNS stimulation system and the PNS stimulation system can be comprised in one stimulation system. Both CNS and PNS can be stimulated at the same time or also intermittently or on demand. These two complementary stimulation paradigms can be combined into one strategy and made available for a patient being equipped with the system. For example, neuromodulation and/or neurostimulation of the CNS may be used to enhance and/or restore the patient's capabilities of movement, especially in a way that the existing ways of physiological signal transfer in the patient's body are supported such that the command signals for body movement or the like still are provided by the patient's nervous system and just supported and/or enhanced or translated by the CNS stimulation system. The stimulation provided by a PNS stimulation system may be used to specifically steer and direct stimulation signals to specific peripheral nervous structures in order to trigger a specific movement and/or refine existing movements. Such a PNS stimulation may be used to refine and/or complete motion and/or movement capabilities of the patient being equipped with the system. It can be e.g. used to complete flexion or extension, lifting, turning or the like of inter alia but not limited to toes, fingers, arms, feet, legs or any extremities of the patient. This can be e.g. done in cases where it is realized that the neuromodulation and/or neurostimulation provided by the CNS stimulation system is not sufficient to complete a movement of the patient. Then, such a movement may be completed or supported by stimulation provided by the PNS stimulation system. The PNS stimulation can be also used to reduce side effects or compensate for imprecisions of the CNS stimulation.

EES can be phasic or tonic, selective PNS stimulation is always phasic. Here, phasic is defined as locked to defined events in the sensing signals (decoded intention, continuous decoding, muscle activity onset, movement onset, event during defined movement (foot off or foot strike during walking for instance).

By PNS stimulation, a stimulation of the upper limb nerves, i.e. the radial, ulnar and/or median nerves can be provided. Also, stimulation of the lower limb nerves like the sciatic and/or femoral nerves can be provided by PNS stimulation. All PNS stimulation can be done by targeting one of the above-mentioned nerves with intra-neural electrodes (transversal or longitudinal) or epi-neural (cuff) electrodes.

By CNS stimulation the following nervous structures may be stimulated: for the upper limb movements the cervical spinal cord or hand/arm motor cortex may be stimulated with the CNS stimulation system. For the lower limb movements, the lumbosacral spinal cord may be stimulated. All these nerves can be targeted with epidural, subdural or intra-spinal/intra-cortical stimulation.

Both PNS and CNS stimulation systems may comprise implantable pulse generators (IPGs).

IPGs can be used for providing the necessary stimulation current and signals for the CNS stimulation system and the PNS stimulation system. The IPG produces the stimulation pulses that are delivered by a lead comprising multiple electrodes to the stimulation site, e.g. the spinal cord.

For EES, the lead is positioned in the epidural space (i.e. on the outside of the dural sac, which encases the spinal cord and the cerebrospinal fluid in which the spinal cord 'floats'), on top of the spinal cord (including but not limited to the segments T12, L1, L2, L3, L4, L5, and S1 bilaterally).

It is also possible that two separated IPGs are provided, one for the PNS stimulation system and one for the CNS stimulation system.

The stimulation parameters for the PNS stimulation and the EES stimulation may be frequency, amplitude, pulsewidth and the like.

Both CNS and PNS stimulations, as well as the combination of these stimulation systems may be used in a sub-motor threshold region, i.e. an amplitude or configuration at which neuronal sensation but no motor response is evoked.

The stimulation may be performed in a closed-loop manner, where feedback is used to adjust the stimulation to movement of the patient, including but not limited to walking or cycling.

Alternatively, the stimulation may also be performed in an open-loop manner, where a pre-defined fixed stimulation is executed without adapting to e.g. the motion of the patient. The stimulation settings may then be determined by the therapist or physiotherapist. The movement of the patient may be recorded.

Control systems may introduce latency and may require prediction to compensate for this latency.

Depending on the control algorithm, the prediction module may be able to predict the patient's motion in order to compensate for the nominal part of the latency of the control system, enabling the system to deliver the correct stimulation in real-time or close to real-time, wherein real-time is defined here that an end-to end latency is less than 100 ms, preferably less than 50 ms.

For instance, for closed-loop walking, the gait phase may be predicted given the current gait phase and cadence.

Similarly, for closed-loop cycling, the pedal phase may be predicted given the current crank angle and angular velocity (both directly provided by placing an IMU on a bicycle crank and/or on one or both feet, directly or indirectly). To ensure that the total latency is kept within limits, the total allowed latency in the control loop (without latency compensation) may be set to a fixed time. To allow for effective latency compensation, the variable part of the latency should be kept as small as possible.

The controller may provide stimulation control signals to the stimulation system on the basis of the information obtained by the sampling module and the prediction provided by the prediction module.

The whole process may be real-time or close to real-time, depending on the amount of filtering, amplifying, and post-processing, and the speed of the connection between the controller and the other subsystems.

Based on among others the motion feedback from the one or more sensors or one or more sensor networks, the control system needs to be able to calculate accurate movement phase, e.g. gait phase and cadence estimates. To do so, in the one or more sensors motion data describing the movement, e.g. of the feet, e.g. acceleration and/or orientation and/or one or more angles and/or angular velocity need to be sampled at a sufficiently high rate and sufficiently low latency, such that the sampled motion data known to the control system closely match the true movement of e.g. the feet. Similarly, data obtained from one or more pressure sensors may be used to calculate the accurate movement phase.

The sampling module may sample motion data at a fixed sampling rate of at least 50 Hz.

The sampling rate may alternatively be at least 75 Hz, especially 100 Hz.

A sampling rate of 100 Hz or more may be required to keep the orientation error due to sampling below 1°. The orientation error quickly rises with reduced sampling rates. As e.g. the range of foot pitch during walking may be small for SCI patients (as small as 20 or 30 degrees), the sensor sampling rate may be ≥100 Hz.

An additional reason for this sampling rate is that a high sampling rate may keep the latency between motion and detection of motion low.

In particular, transmitting raw acceleration (3 floating point numbers) and angular velocity (3 floating point numbers) together with the orientation (4 floating point numbers in quaternion format) may lead to packet payloads of 20 bytes at 16 bits precision (which is the measurement resolution of a state-of-the-art OTS available IMU).

Because the motion of the bicycle crank during cycling is smoother than the motion of the foot during walking (for instance, there are no high impacts due to the absence of foot strikes), a sampling frequency of 100 Hz may be also sufficient for cycling.

The control system may allow an overall latency budget, the latency budget being distributed to one or more subsystems and/or interfaces of the control system.

Possible latency sources include but are not limited to the one or more sensors, the controller, and the stimulation system, as well wireless or wired connections between these modules. In particular, the possible sources of latency include but are not limited to: sensor sampling, sensor data processing, sensor data transmission to the controller, sensor data processing at the controller, generation of new stimulation input from by the controller, stimulation data transmission to the stimulation system, implementation of the stimulation input by the stimulation system.

This total allowed latency without compensation may include latencies due to processing and communication over the various interfaces, but also latencies due to sampling and communication at finite rates.

The allowed overall latency budget may be 100 ms or less, especially 50 ms or less.

Further, the subsystems may include at least one of a sensor (as described above), a controller, a pulse generator, a sensor network, a programmer, a communication module, a telemetry module.

The sensors may be battery powered, body worn sensors (directly or indirectly), collecting motion data, and sending it to the controller. Their intended use is to capture body motion parameters.

The controller may be a battery powered, body worn device (directly or indirectly), receiving data from sensor(s) and able to send stimulation commands to the IPG for specific tasks (i.e. an activity/training exercise). Its intended use is to determine optimal stimulation settings for any given task and providing this information to the IPG. The controller may control the stimulation provided by the CNS-Stimulation system and/or the PNS-Stimulation system on the basis of data provided by the one or more sensors and/or one or more sensor networks.

There may be a programmer. The programmer, or also called the clinician programmer, can be used to receive inter alia stimulation parameter, patient data, physiological data, training data etc.

It may comprise a Space Time Programmer (STP) for e.g. programming spatial and temporal parameters of the stimulation, a Physiotherapist Programmer (PTP) for e.g. allowing the physiotherapist adjustment to the stimulation, and a Patient Programmer (PP) for e.g. allowing the patient to select a specific stimulation program.

The Space Time Programmer (STP), Physiotherapist Programmer (PTP), and Patient Programmer (PP) can be embodied as applications installed on a mobile device that communicate with the controller. They are used by the treating physician (TP), a physiotherapist (PT), or the Patient to provide inputs to the controller, e.g., selecting, starting, and stopping a task or configuring stimulation parameters.

The programmer can allow adjusting the stimulation parameters of a task, while the task is running. This enables the user to tune the stimulation without having to start and stop the task, which would be very cumbersome at the start of the rehabilitation training, when all stimulation partitures are developed and tuned.

Generally speaking, the programmer may have the following structure:

In a first embodiment, the programmer can be embodied such that it is possible to receive inter alia but not limited to stimulation parameters, patient data and the like, check and/or reprogram the stimulation settings and send it back to e.g. the controller.

The programmer is in this first embodiment capable to receive data from the controller, display data, receive input from the user and then send it back to the controller. In other words: the programmer can receive, process and re-send the data.

In a second embodiment, the programmer may receive data from a remote database. The database may be e.g. linked with the stimulation system via a separate interface, which is configured for data transfer from the system to the database only.

The programmer is in this second embodiment capable to receive data from the remote database, display data, receive input from the user and then send it to the controller. In other words: the programmer is only in connection with the controller for sending data, it does not receive data from the controller or any implanted system parts.

There may be a pulse generator. The pulse generator may be an implantable pulse generator (IPG) or the like. The IPG may be a battery powered device that generates the electrical stimulation, subcutaneously implanted. Its intended use is to deliver electrical stimulation to a lead based on command received from the controller.

There may be a communication module WSN. The communication module WSN may be a wireless link between the sampling module and the controller, as well as between the prediction module and the controller, as well as between the one or more sensor(s) and the sampling module, as well as between the one or more sensor(s) and the prediction module. Based on the motion feedback from the one or more sensor(s), the controller needs to be able to provide accurate gait phase and cadence estimates. Hence, the motion data needs to be sampled and transmitted at a sufficiently high rate, such that the sampled motion signals known to the controller closely match the true motion of the feet. For example, a sampling rate of ≥100 Hz may be required for accurate gait phase estimation, also a communication rate of ≥100 Hz may be required for the WSN link. Choosing a lower communication rate would either lead to loss of valuable information (when only one measurement sample is transmitted at a time) or would lead to high latencies as measurement samples have to wait for the next transmission time to be transmitted.

There may be a communication module COM. The communication module COM may be a wireless link between the programmer and the controller. During tasks COM may be only used in the control loop for providing stimulation partiture updates to the controller, and to start and stop the task.

There may be a telemetry module TEL. The telemetry module TEL may be a wireless link between the controller and the stimulation system. TEL may send data from the controller and receive by the stimulation system. This also may include error-correction, retries, etc. The subsystem TEL may communicate commands including but not limited to or stopping the task.

The telemetry module TEL may be or may comprise a near field magnetic induction module (NFMI).

The controller may have an allowed latency budget of approx. 10-15 ms, especially approx. 11-13 ms, preferably approx. 12 ms.

In particular, potential latency sources of the controller may be processing of data from the sampling module and the preprocessing module, executing of control algorithm(s), and delivering one or more stimulation updates to the telemetry module TEL.

Moreover, the telemetry module TEL may have an allowed latency budget of approx. 5-10 ms, especially approx. 6-8 ms and preferably approx. 7 ms, especially wherein out of the 7 ms a larger part of the latency budget may be for waiting time for establishing a telecommunication link and a smaller part of the latency budget may be a buffer to accommodate with the technological natural latency of the near field magnetic induction module (NFMI).

In particular, potential latency sources of the telemetry module TEL may include but are not limited to sending and/or receiving and/or acknowledging data from the controller by the IPG, correcting errors, retries and the like.

The sensor network may be a wireless sensor network. This wireless network WSN may link the two or more sensors of the sensor network and the controller.

The sensor network may have an allowed latency budget of approx. 15-20 ms, especially approx. 16-18 ms, preferably approx. 17 ms.

In particular, potential latency sources of the sensor network may include but are not limited to sampling of raw measurement data at a fixed rate of e.g. 100 Hz or higher, analog-to-digital conversion, filtering, post-processing, delivering of clean data to an interface.

The pulse generator may have an allowed latency budget of approx. 0.1-3.0 ms, especially approx. 1.5-2.5 ms, preferably approx. 2.0 ms.

In particular, potential latency sources of the pulse generator may include but are not limited to processing data received from the controller, checking potential errors, and updating stimulation parameters.

The prediction module may be linked to or may be part of the controller.

The prediction module may be connected directly and/or indirectly with at least one sensor and/or a/the sensor network. Further, the prediction module may be configured and arranged to predict patient motion and/or movement on the basis of sensor input data, especially to manage the latency of the control system in order to stay within an overall allowed latency budget.

Further, there may be a latency budget monitoring and/or management system, which may be configured and arranged to monitor and manage the overall latency of the control system by monitoring and/or managing latency of subsystems of the control system, especially online and/or in real-time.

The control system may be a closed-loop system.

The control system may alternatively be an open-loop system.

In particular, sensor feedback may be used to synchronize the stimulation to the motion of the patient.

In particular, for closed-loop walking, feedback may be used to adjust the stimulation to the gait phase of the patient.

In particular, for closed-loop cycling, feedback may be used to adjust the stimulation to the pedal phase of the patient. The pedal phase may be predicted given the current crank angle and angular velocity (both may be directly provided by placing an IMU on a bicycle crank or on at least one foot of the patient).

Furthermore, the control system may comprise a pre-warning module, which is configured and arranged to provide a pre-warning signal indicative of providing an upcoming stimulation event.

Regulating the gait to a predefined reference interferes with voluntary motion of the patient. In particular, voluntary motion of the patient may have a large effect on the movement, as the patient's voluntary control may modulate muscle activation. The movement pattern may therefore differ from comparable to a healthy subject, to impaired or reduced despite identical stimulation. The pre-warning signal may help the patient to adjust voluntary control to the respective movement planned, thus a smooth movement may be performed. The pre-warning signal may include but is not limited to a sound signal, vibration, light signal, smell, taste, pain, temperature (warm, cold), humid signal, draught or the like, or sub-motor threshold stimulation.

The system may be also applied for a patient being supported by an external device, including but not limited to body-weight support, a walker, or crutches.

BRIEF DESCRIPTION OF DRAWINGS

Further details and advantages of the present invention shall now be disclosed in connection with the drawings.

It is shown in

FIG. 3 a table specifying the nerve fiber types, diameters, and function;

FIG. 5 a table specifying the intended movement and the involved agonist muscle and the involved antagonist muscle;

FIG. 6 discrete sets of functional muscle blocks (FMB) and custom muscle blocks (CMB);

DETAILED DESCRIPTION

Note that in the following we primarily refer to CNS/EES stimulation. The one skilled in the art may transfer the stimulation parameters to PNS/FES stimulation.

Figure 1:
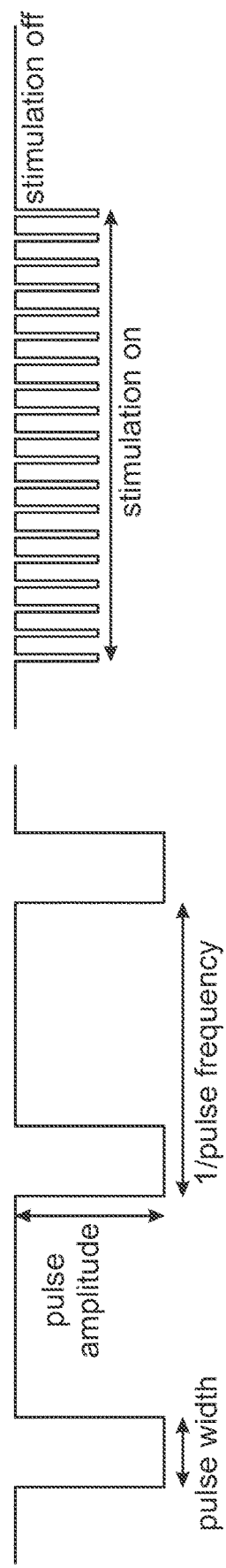
FIG. 1 a schematic, very simplified representation of a stimulation pulse delivered by a system according to the present invention.

The control system may provide stimulation data for movement reconstruction and/or restoration for stimulation of afferent nerve fibers using electrical current pulses. Given this starting point, the following stimulation parameters may be identified:

electrode configuration (which electrodes to use, polarity)
stimulation (Pulse) amplitude
stimulation (Pulse) width
stimulation (Pulse) frequency FIG. 1 illustrates a schematic, very simplified representation of the stimulation pulse, which illustrates the pulse amplitude, pulse width, and pulse frequency. Each stimulation pulse may be followed by a neutralization pulse or a neutralization period (not depicted) to remove the electric charge from the tissue in order to avoid tissue damage.

The effects of each of the stimulation parameters are described below.

Electrode configuration: Stimulating a specific muscle group requires applying a specific electrical field at a specific location on the spinal cord. Therefore, in the present control system the electrical stimulation may be delivered to the spinal cord by a lead with multiple electrodes. The location, shape, and direction of the electrical field that is produced may be changed by choosing a different electrode configuration (which electrodes are used, with which polarity and potential) that is used to deliver the current. Hence, the electrode configuration may determine to which spinal roots the stimulation is delivered, and therefore which subsequent muscles or muscle groups activity will be reinforced.

Figure 2A:
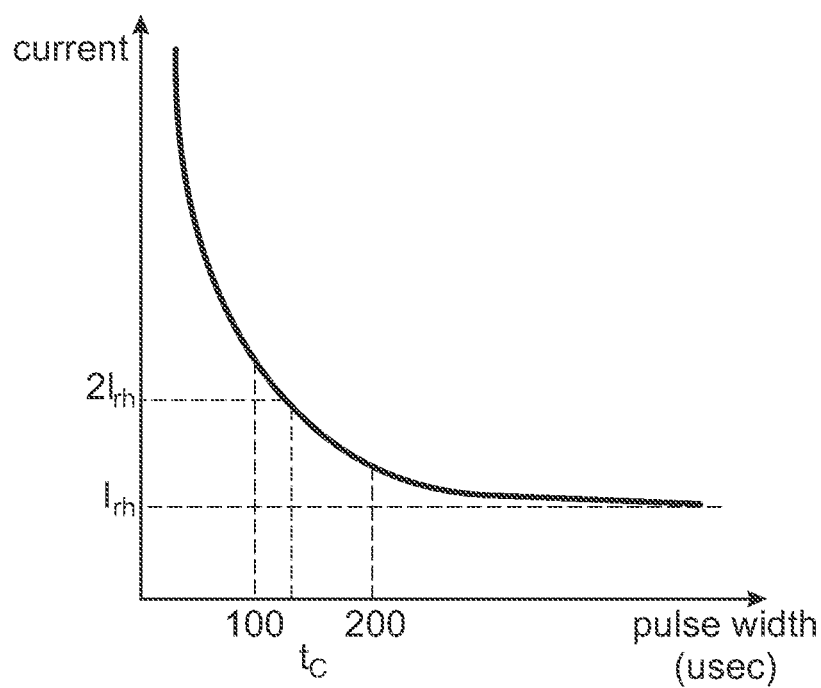
FIG. 2A, B the necessary current and necessary charge to trigger an action potential in a nerve fiber as a function of the pulse width (using a square pulse)
Figure 2B:
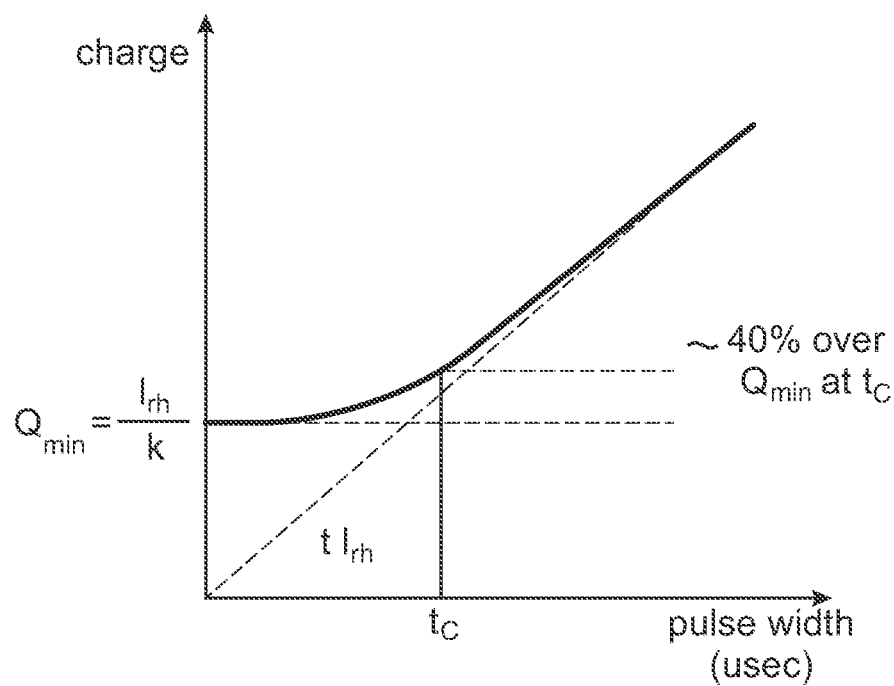

Pulse amplitude and pulse width: In FIG. 2A and FIG. 2B the necessary current and necessary charge to trigger an action potential in a nerve fiber are shown as a function of the pulse width (using a square pulse) (cf. Merrill D R., et al. *Electrical Stimulation of excitable tissue: design of efficacious and safe protocols, J Neurosci methods* 141(2): 171-98 (2005)). FIG. 2A and FIG. 2B also show the rheobase current $I_{rh}$, which is the current that is required when using infinitely long pulse widths, and the chronaxie time $t_c$, which is the required pulse width at a current of $2I_{rh}$.

Although larger currents may be required at smaller pulse widths, the total required charge may decrease with decreasing pulse width, see FIG. 2B. Hence shorter pulses with higher current amplitudes may be energetically beneficial.

For smaller diameter nerves, the current-pulse width curve of FIG. 2A shifts, as smaller diameter fibers may require higher currents. Hence, a higher current may activate more nerve fibers, as also smaller diameter nerve fibers may be activated (until saturation). However, also cross-talk is increased as also more neurons from neighboring roots may be activated. Fortunately, the afferent fibers involved in motor control (fiber types Ia and Ib) may be all relatively large (12-20 µm), while the fibers involved in touch, temperature, and pain feedback (which should not be triggered) may be relatively small (0.5-12 µm), as depicted in FIG. 3. Hence, with increasing pulse width and/or current amplitude, the type Ia and Ib fibers may be the first to be recruited. This may enable recruiting (most of) the relevant fibers while keeping cross-talk and patient discomfort to a minimum.

Pulse frequency: The pulse frequency may determine the frequency of the action potentials generated in the afferent nerves, assuming sufficient charge is delivered each pulse to trigger the action potentials. As no new action potential can occur in a nerve during the refractory period, the frequency of the triggered action potentials will saturate at high pulse frequencies. This saturation point is generally at around 200 Hz for afferent fibers (Miller J P. et al., *Parameters of Spinal Cord Stimulation and Their Role in Electrical Charge Delivery: A Review. Neuromodulation: Technology at the Neural Interface* 19, 373-384, (2016)). However, stimulation at frequencies above the saturation point may still be beneficial, as by increasing frequency the total charge delivered per unit time (i.e. charge per second) can be increased without changing current amplitude or pulse width (Miller J P. et al., *Parameters of Spinal Cord Stimulation and Their Role in Electrical Charge Delivery: A Review. Neuromodulation: Technology at the Neural Interface* 19, 373-384, (2016)).

Pulse positioning: Many tasks, including walking, require simultaneous activation of multiple muscle groups. Hence, to support these Tasks, multiple muscle groups may need to be stimulated simultaneously, each requiring a specific electrical field and pulse frequency. When applied simultaneously, these different electrical fields may interact with each other, potentially leading to unintended and uncontrolled effects. Therefore, to avoid this situation, care should be taken that the individual stimulation pulses and their neutralization periods targeting different muscle groups are not applied simultaneously. This may not be considered a stimulation parameter but does identify a required system feature: a pulse positioning algorithm (PPA).

The previous section describes the effect of the stimulation parameters on triggering action potentials in afferent nerve fibers. Although triggering these action potentials is an essential step in the therapy, in the end the stimulation should enable or support the patient in performing specific lower body motions, which may require the activation of specific muscles or muscle groups. The effect of the triggered action potentials in afferent nerve fibers on muscle activation may be filtered inside the spinal cord through spinal reflex circuits and modulated through the voluntary control of the patient. Hence, the effect of the stimulation parameters on muscle activation may be not perfectly clear and may be affected by intra- and inter-Patient variations. The following aspects may be of relevance here:

different patients may have different levels of voluntary control over their lower body, depending on the type and severity of their SCI lesion level and state of (spontaneous) recovery.

stimulation of afferent nerve fibers may assist or enable activation of the corresponding muscles but may not necessarily enforce motion. The patient may modulate the activation (e.g. make a large or small step without changing the stimulation), or even resist motion of the leg completely. This may vary per patient and may change with increasing recovery.

conjecture: Because the spinal cord floats in the cerebrospinal fluid, the distance between the spinal cord and the lead electrodes may vary (mostly as a function of the patient's posture: prone—large distance, supine—small distance). Another hypothesis may be that due to posture changes, the layer thickness of low conductive epidural fat between the lead electrodes and the dura/cerebrospinal fluid a changing, leading to an impedance change as seen by the electrodes, and resulting in an altered current/voltage delivered stimulation by the electronics. As a result, the effect of the applied stimulation (including muscle onset and saturation) may also vary with the patient's posture. Although this conjecture is not proven, patients may successfully make use of the described effects to modulate the stimulation intensity by varying their posture: bending forward reduces the intensity, bending backward increases it.

pulse frequencies between 40 and 120 Hz may mostly being used, although it may theoretically be possible to stimulate up to 500 Hz as this may have benefits for selectivity in muscle activation and improved voluntary control of the patient.

It may be possible that general increasing the pulse amplitude may not lead to increased recruitment of muscle fibers (with corresponding increased cross-talk), and that increasing the stimulation frequency may lead to increased muscle activation without affecting cross-talk. However, increasing the stimulation frequency may reduce the intensity of natural proprioception and result in a decreased feeling in the leg of the patient. This is probably due to the collision of natural sensory inputs with antidromic action potentials generated by the electrical stimulation. At high frequency (above 100 Hz), patients may even report a complete loss of sensation of the leg and "feel like walking with their legs being absent". This is a non-comfortable situation requiring the patient to make a leap of faith at each single step, believing that the leg that he/she does not feel anymore will support him/her during the next stance phase. Adjusting the balance between stimulation amplitude and frequency may therefore be necessary to find the optimal compromise between cross-talk limitation and loss of sensation. Simulations suggest that a possible workaround may be to shift the stimulation domain to lower amplitudes and even higher frequency, such that with a minimal number of stimulated fibers the same amount of activity is triggered in the spinal cord. Such hypothesis requires validation via additional clinical data. Finally, it may also be identified that different patients require different stimulation, i.e. that the optimal frequency and amplitude settings may vary highly between patients. Hence, the relation between stimulation amplitude and frequency on muscle activation may be still for a large part unclear. Moreover, the optimal stimulation settings may vary during the day, the assistive device that is used (including but not limited to crutches, walker, etc.), over time with improved recovery, and with the goal of the training or activity.

Timing: Apart from applying the correct electrical field at the right location on the spinal cord, they also may need to be applied at the correct moments in time and correctly sequenced. The relevant timing aspects that are identified are listed below.

Figure 4:
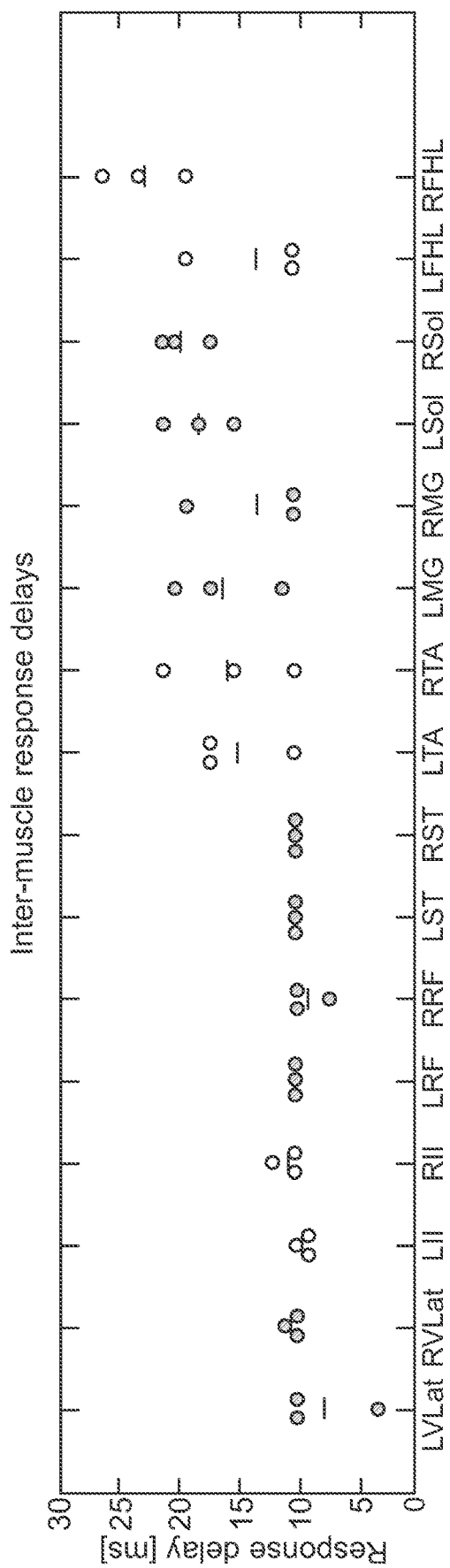
FIG. 4 the delay between electrical stimulation of the spinal cord and the evoked muscle response for various leg muscles.

There is a delay from stimulation on the spinal cord to muscle activation (typical values in the order of 0-30 ms depending on the muscle, see FIG. 4, LVLat=left vastus lateralis, RVLat=right vastus lateralis, Lll=left iliopsoas, Rll=right iliopsoas, LRF=left rectus femoris, RRF=right rectus femoris, LST=left semitendinosus, RST=right semitendinosus, LTA=left tibialis anterior, RTA=right tibialis anterior, LMG=left medial gastrocnemius, RMG=right medial gastrocnemius, LSol=left soleus, RSol=right soleus, LFHL=left flexor halluces longus, RFHL=right flexor halluces longus).

while EES enables patients to perform motions, the patient may need to be able to predict when the stimulation will occur in order to make the best use of the stimulation. Likewise, suppressing motion while stimulation is provided also requires that the patient knows when to expect the stimulation. Hence, predictability of the stimulation timing is essential.

when the stimulation is not synchronized to the patient's (intended) motion, the patient may not be able to perform a proper movement. Here, this may mean that the stimulation needs to be predictable by the patient, as the patient needs to synchronize to the stimulation.

the duration of the stimulation for leg swing during walking may need to be finely tuned. For some patients, increasing the duration of this stimulation by 100 ms made the patient jump instead of performing a proper step.

20 ms may be a sufficient resolution for tuning the stimulation timings (i.e. the on/off times of the stimulation for a specific muscle group may not need to be controlled at a precision below 20 ms). Given current data availability, controlling the timings at resolutions below 20 ms may not seem to improve the effectiveness of the stimulation.

Based on the previous sections, the stimulation parameters may be selected to control in the control system. This may determine the control output space that is used, and therefore the complexity of the control problem and the potential effectiveness of the control system.

First it is discussed which parameter spaces can be reduced or eliminated. The remaining control output space is summarized below.

Electrode configuration: Walking, as well as other movements of the lower extremities, may be composed of well-coordinated flexion and extension of lower body joints by contraction of agonist muscles and relaxation of antagonist muscles. The specific set of agonist and antagonist muscles for joint specific flexion and extension may be grouped, and as the number of joints is limited, this means that only a small discrete set of muscle groups may be needed to be stimulated. For each joint flexion and extension, the STP for e.g. for e.g. programming spatial and temporal parameters of the stimulation will support creating the optimal electrode configuration for activation of the agonist muscles while avoiding activation of the antagonist muscles (as well as avoiding activation of muscles on the contralateral side). This may be done in a procedure called the functional mapping. We define the Functional Muscle Blocks (FMB), as the resulting stimulation configurations for each specific muscle group. At least 12 specific FMBs have been identified for using the control system, these are listed in FIG. 5 with their corresponding agonists and antagonists.

As knee flexion and hip extension both involve the semitendinosus, it is physically not possible to target knee flexion and hip extension separately. Therefore, FIG. 5 does not include knee flexion (this could be considered redundant to hip extension).

Next to the 12 FMB listed in FIG. 5, it is also envisioned that the trainer/therapist/physiotherapist may create Custom Muscle Blocks (CMB). Creating CMB may be useful in case the trainer/therapist/physiotherapist wants to apply stimulation that does not specifically target any of the 12 muscle groups targeted by the FMB, or in case the trainer/therapist/physiotherapist wants to use a variant of one of the 12 FMB in a specific task.

Hence, by limiting the electrode configurations to the discrete set of FMB and CMB (versus an infinite number of possible electrode configurations), the control problem complexity may be reduced considerably without significantly affecting the potential effectiveness of the control system. Stimulation for a Task is then reduced to stimulation of (a subset of) the predefined FMB and CMB, see FIG. 6. In this example, the Right Trunk Stability is used in both Task 1 and Task 2.

The functional mapping procedure may require measuring the response of each of the muscles listed in FIG. 5 with EMG sensors. Due to the large number of muscles, this requires attaching many EMG sensors to the patient (which is time consuming) and processing a large amount of data. Moreover, as motion of the patient may induce signal artifacts, the functional mapping may be best performed while the patient is not moving. For these reasons, the functional mapping procedure may be performed in a separate session using the Space Time Programmer for e.g. programming space and time of the stimulation, and not e.g. adaptively within the control system. Hence, the configuration of FMB and CMB may be considered as a given to the control system.

Pulse width: From the viewpoint of triggering action potentials in afferent nerve fibers, the parameters pulse width and pulse amplitude may be tightly linked and may together determine which afferent nerve fibers are recruited. Increasing the pulse width may allow to reduce the amplitudes and decreasing the pulse width may allow reducing energy consumption (as the total required charge for triggering an action potential decreases with decreasing pulse width, see FIG. 2B and stimulating more FMB simultaneously or at higher frequencies. However, from a control perspective the two parameters may be (almost) redundant, as increasing either parameter may lead to the recruitment of more afferent nerve fibers over a larger area.

Pulse widths below chronaxie time $t_c$ may quickly require high currents (and thus high voltages), which is difficult to produce and may lead to patient discomfort. Beyond $t_c$, the strength-duration curve of FIG. 2A is almost flat, so increasing pulse width beyond $t_c$ has little effect on the required amplitudes while it increases total power consumption. Also considering that having a fixed pulse width simplifies the pulse positioning, the pulse width is chosen to be fixed (at a value near chronaxie time $t_c$ such that both energy consumption and required current amplitudes remain low, where $t_c \approx 200$ μs for afferent dorsal root nerve fibers in humans). This reduces the complexity of the control problem by reducing the number of output parameters.

This may leave the following stimulation parameters to be controlled over time by the control system:
which FMBs to stimulate
stimulation amplitude per FMB
stimulation frequency per FMB The pulse positioning may be considered a lower level problem and may therefore be not a direct output of the control system (system feature). The pulse positioning may be performed by the IPG.

Although combining amplitude and frequency to a single 'intensity' parameter has been considered, doing so may not be envisioned for the control system, as these parameters may have very different effects. On triggering action potentials in afferent nerve fibers, the amplitude and frequency may be independent parameters: the amplitude determines in which afferent nerve fibers action potentials are triggered, the frequency determines the rate at which they are triggered. Hence, in principle the amplitude determines which muscle fibers are activated, the frequency determines how hard, although it is unclear if the independence of the two parameters also holds for muscle activation due to the signal processing that occurs in the spinal cord. Moreover, it may be apparent that for some patients changing the amplitude gives the best results, while for other patients the frequency may be the more useful parameter.

As the precise relation between frequency and amplitude is not known in the clinical context it may not be recommended to combine frequency and amplitude to single parameter. Hence, the stimulation frequency and amplitude may be controlled independently from each other.

Figure 7:
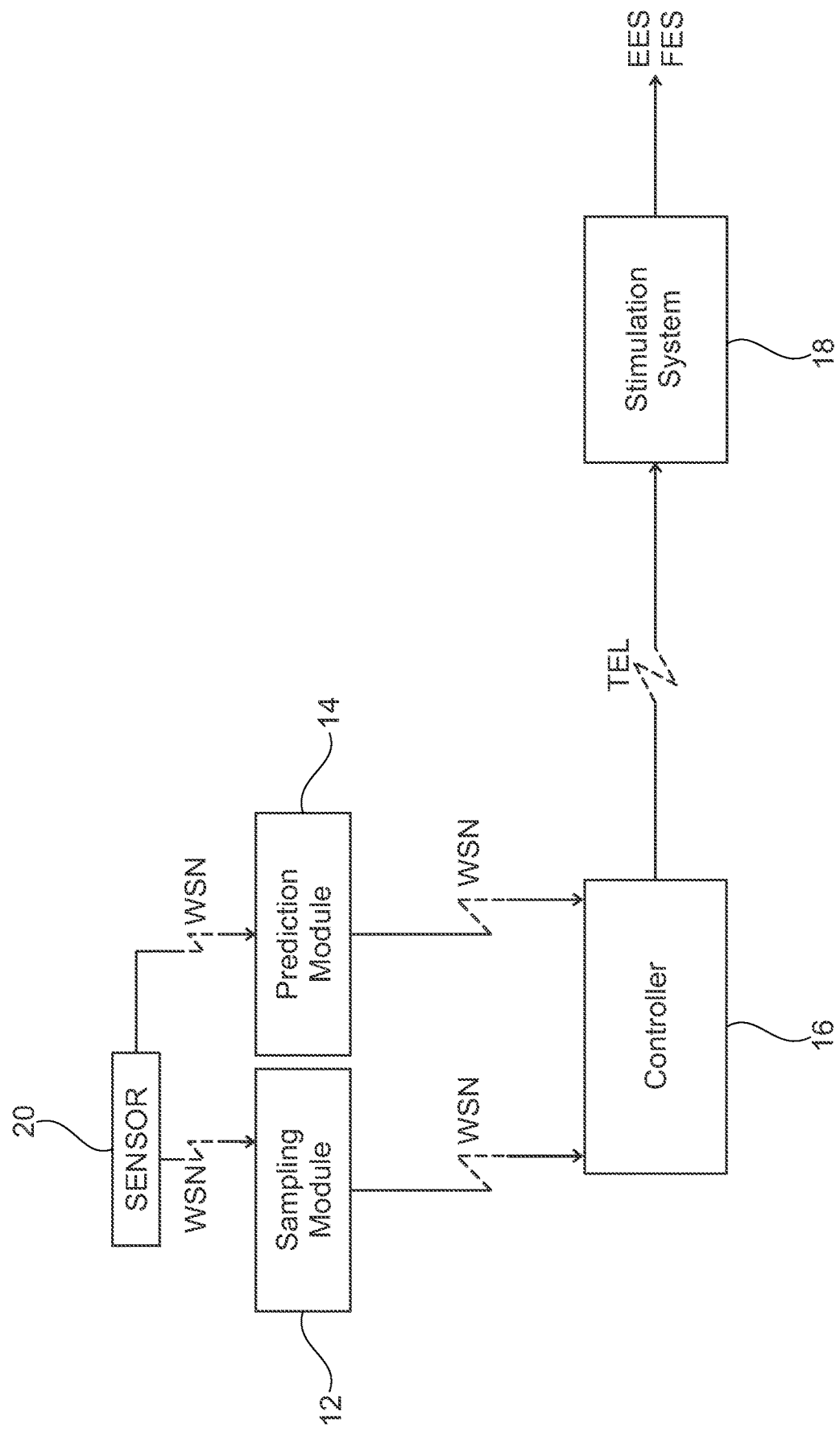
FIG. 7 a general layout of an embodiment of the control system for a movement reconstruction and/or restoration system for a patient according to the present invention.

FIG. 7 shows a general layout of an embodiment of the control system 10 for a movement reconstruction and/or restoration system for a patient according to the present invention.

The control system 10 comprises a sampling module 12.

Additionally, the control system 10 comprises a prediction module 14.

In the shown embodiment, the control system 10 further comprises a controller 16. Furthermore, the control system 10 comprises in the shown embodiment a stimulation system 18.

In this shown embodiment, the stimulation system 18 comprises a pulse generator, in particular an implantable pulse generator.

In this shown embodiment, the stimulation system 18 comprises both a CNS stimulation system for CNS stimulation and a PNS stimulation system for PNS stimulation.

However, the stimulation system 18 could also only comprise a CNS stimulation system for CNS stimulation or a PNS stimulation system for PNS stimulation.

In this embodiment, the control system 10 further comprises a subsystem, in particular a sensor 20.

In this embodiment, the control system 10 further comprises another subsystem, in particular a telemetry module TEL.

The telemetry module TEL could be or could comprise a near field magnetic induction module (NFMI).

Possible embodiments of other subsystems that could be generally comprised in the control system 10 comprise at least one of a controller and/or a pulse generator and/or a sensor network and/or a programmer and/or a communication module COM.

However, the control system 10 could also not comprise any other subsystem.

In this embodiment, the sensor 20 is connected to the sampling module 12.

The sensor 20 is also connected to the prediction module 14.

The connection between the sensor 20 and the prediction module 14 could generally be a bidirectional connection.

Alternatively, and/or additionally, a sensor network could be connected to the prediction module 14.

The connection between the sensor 20 and/or the sensor network and the sampling module 12 is in the shown embodiment a direct connection.

However, also an indirect connection (i.e. with another component of the control system 10 in between) would be generally possible.

The connection between the sensor 20 and the sampling module 12 is established in the shown embodiment via a wireless network WSN.

However, also a cable-bound connection would be generally possible.

The connection between the sensor 20 and the prediction module 14 is in the shown embodiment a direct connection.

This connection could generally be a bidirectional connection.

Alternatively, and/or additionally, a sensor network could be connected to the prediction module.

However, also an indirect connection (i.e. with another component of the control system 10 in between) would be generally possible.

The connection between the sensor 20 and/or the sensor network and the prediction module 14 is established in the shown embodiment via a wireless network WSN.

However, also a cable-bound connection would be generally possible.

The sampling module 12 is connected to the controller 16.

The connection between the sampling module 12 and the controller 16 is in the shown embodiment a direct connection.

However, also an indirect connection (i.e. with another component of the control system 10 in between) would be generally possible.

The connection between the sampling module 12 and the controller 16 is established in the shown embodiment via a wireless network WSN.

However, also a cable-bound connection would be generally possible.

However, the sampling module 12 and the controller 16 could also be implemented in the same system.

The prediction module 14 is connected to the controller 16.

The connection between the prediction module 14 and the controller 16 is in the shown embodiment a direct connection.

However, also an indirect connection (i.e. with another component of the control system 10 in between) would be generally possible.

The connection between the prediction module 14 and the controller 16 is established in the shown embodiment via a wireless network WSN.

However, also a cable-bound connection would be generally possible.

However, the prediction module 14 and the controller 16 could also be implemented in the same system.

In an alternative embodiment, the prediction module 14 could be part of the controller 16.

The controller 16 is connected to the stimulation system 18.

The connection between the controller 16 and the stimulation system 18 is in the shown embodiment a direct connection.

However, also an indirect connection (i.e. with another component of the control system 10 in between) would be generally possible.

The connection between the controller 16 and the stimulation system 18 is established in the shown embodiment via a wireless link, i.e. a telemetry module TEL.

However, also a cable-bound connection would be generally possible.

In the present embodiment, a patient is equipped with the present control system 10.

In this embodiment, the control system 10 is body worn.

By means of one or more sensors 20, signals indicative for a movement, e.g. movement of position of the body and/or parts of the body, including but not limited to the trunk and/or the head and/or a limb, e.g. an arm or leg, and/or a foot or hand, e.g. during walking, cycling, swimming, rowing, stepping, or running, can be sensed and used by the control system 10.

In this embodiment, signals indicative for walking are sensed by the sensor 20.

The sensor signals are transferred to the sampling module 12.

In other words, the sampling module 12 samples data from the sensor 20.

In general, the sampling module 12 samples data at a sampling rate of at least 50 Hz.

In this embodiment, the sampling module 12 samples data at a fixed sampling rate of 100 Hz.

In an alternative embodiment, the sampling module 12 samples data at a fixed sampling rate of 50 Hz.

In another alternative embodiment, the sampling module samples data at a fixed sampling rate of 75 Hz.

However, also every other sampling rate could be generally possible.

In general, the optimal sampling rate could be calculated following the Nyquist-Shannon sampling theorem.

Alternatively, the optimal sampling rate could be at least 5 to 10 times the highest significant frequency present in the analog signal.

The data from the sampling module 12 are transferred to the controller 16 and there processed.

The prediction module predicts motion and/or movement of the patient on the basis of sensor 20 input data, especially to manage and/or monitor latency of the control system 10 in order to stay within an overall allowed latency budget.

The prediction module 14 may compensate for the latency introduced by the control system 10.

Depending on the control algorithm, the prediction module 14 could be able to predict the patient's motion in order to compensate for the latency in the closed-loop.

In other words, the prediction module 14 adds latency to compensate for the nominal part of the latency of the control system 10 and enables real-time, or close to real-time, synchronization of stimulation to the patient's motion.

For instance, for closed-loop walking, the gait phase could be predicted given the current joint angle and angular velocity provided by placing one or more sensors 20 directly or indirectly on one or both feet and/or legs and/or the abdomen and/or trunk of a patient.

The data and/or information from the prediction module 14 are transferred to the controller 16.

The controller 16 provides stimulation control signals to the stimulation system 18 on the basis of the information obtained by the sampling module 12 and the prediction provided by the prediction module 14.

In other words, the controller 16 processes data from the sampling module 12 and the prediction module 14.

By means of the controller 16, the control software is executed. The controller 16 programs the stimulation system 18 comprising the implantable pulse generator to deliver the correct stimulation to the patient via the stimulation system 18, in particular the implantable pulse generator.

In this embodiment, the stimulation system 18 functions as CNS stimulation system, in particular EES-system and as PNS stimulation system, in particular FES-system.

There may be also a programmer (not shown in the figures). The programmer, or also called the clinician programmer, can be used to receive inter alia stimulation parameters, patient data, physiological data, training data etc.

Not shown in FIG. 7 is that the at least one sensor 20 is an inertial measurement unit (IMU) 20.

Said IMU 20 comprises an accelerometer, a gyroscope, and a magnetometer.

Said IMU 20 measures and reports 3D accelerations, 3D angular velocities and 3D orientation using a combination of an accelerometer and a gyroscope.

In an alternative embodiment, an IMU 20 could use a combination of one or more of an accelerometer, one or more gyroscopes, and optionally one or more of a magnetometer.

By integrating the angular velocity assessed by the gyroscope and fusing with data from the accelerometers, a precise measurement of the angle of the foot is obtained.

Based on these measurements the orientation of the IMU 20 with respect to the fixed world is estimated accurately, using standard sensor fusion algorithms.

So, movement is detected and therefrom also a signal derived, which is indicative for an angle, e.g. the foot angle.

Real-time and non-real-time reconstruction of foot trajectories may be done up to a few centimeters accuracy.

In an alternative embodiment, at least one sensor 20 could also be one of an optical sensor, a camera, a piezo element, a velocity sensor, an accelerometer, a magnetic field sensor, a torque sensor, a pressure sensor, a displacement sensor, an EMG measurement unit, a goniometer, a magnetic position sensor, a hall sensor, a gyroscope and/or one or more motion tracking video cameras, or one or more infra-red cameras.

Some sensors 20 could require fixed base station in the environment, including but not limited to magnet sensors or infra-red sensors.

Electromagnetic position sensors, optical sensors and cameras could estimate 3D position and orientation.

Torque sensors could be placed on a bicycle crank for assessing the torque during cycling.

Some sensors 20 could be worn by the patient without acquiring fixed base station, including but not limited to piezo elements, pressure sensors and/or torque sensors.

By directly and/or indirectly attaching one or more sensors 20, e.g. IMUs 20, to the trunk and/or waist and/or at least one limb and/or one or more parts of a limb, including one or more joints, the angular velocity and angle of one or more limbs and/or one or more parts of limbs and/or one or more joints during motion, e.g. gait cycle could be determined to realize the reorganization of the various motion phases, e.g. gait phase.

Thanks to the angle it could be possible to compute the acceleration of the limb and/or part of the limb in the forward direction.

However, also acceleration in any other direction may be determined.

In particular, the angle of the ankle joint varies during gait cycle with different gait events, including but not limited to pre-swing, swing, loading response and stance (and/or toe-off, midswing, heel strike, foot flat and midstance).

The angle of at least one limb and/or part of a limb (including one or more joints) of a patient could be used by the prediction module 14 to predict the intended and/or ongoing motion.

The angle of at least one limb and/or part of a limb can also be used to find out which support the patient really needs from the control system 10.

For open loop walking, a change in limb angle and/or part of a limb angle (including joints, e.g. ankle joint) over a certain threshold could be used to initiate a certain stimulation sequence.

In particular, the gait event heel-off could trigger the stimulation for one or more complete gait cycles.

However, also other gait events, including but not limited to pre-swing, swing, loading response and stance (and/or toe-off, midswing, heel strike, foot flat and midstance) could trigger stimulation for one or more complete gait cycles.

Note that also single events of other periodic movements (including but not limited to cycling, rowing, swimming, stepping, standing up, sitting down) could trigger the stimulation for one or more complete motion cycles.

In other words, the control system 10 is not only applicable for walking/gait cycle, but also for diverse other movements including but not limited to cycling, rowing, swimming, stepping, standing up, sitting down.

Two or more sensors 20 could form a sensor network.

In general, the sensor network could be a wireless sensor network.

However, also a cable-bound connection between the single units of a sensor network could be generally possible.

In an alternative embodiment, the control system 10 could be connected to a training entity via a wireless link.

Note that the prediction and reconstruction of the movement could be relevant for the training entity, including but not limited to a body weight support robot or a bicycle.

Note that the body weight support could be adapted, or the cycling cadence could be adapted based on the movement reconstruction.

Not shown in FIG. 7 is the fact that the one or more sensors 20 could be connected to, inserted and/or integrated in a training entity, included but not limited to an exoskeleton, body weight support, treadmill and/or crutches.

Not shown in FIG. 7 is that for closed-loop cycling, measuring the pedal phase can simply be achieved by attaching a sensor 20, e.g. an IMU, to the crank of the bicycle.

Angles could be reflected in the position of the pedal.

The pedal phase could then be defined as the crank angle, which is directly linked to the IMU orientation.

Note that the pedal phase could also be predicted given the current crank angle and angular velocity (both directly provided by placing an IMU on a bicycle crank).

For closed-loop cycling, the stimulation partiture defines spatial stimulation, stimulation at which pedal phase, amplitudes, and frequencies.

Not shown in FIG. 7 is the total latency budget of the control system 10.

The control system 10 could allow an overall latency budget, the latency budget being distributed to one or more subsystems of the control system 10.

Not shown in FIG. 7 is that the control system 10 could further comprise a latency budget monitoring and/or management system.

The latency budget monitoring and/or management system could be configured and arranged to monitor and manage the overall latency of the control system 10 by monitoring and/or managing latency of subsystems of the control system 10, especially online and/or in real-time.

The total latency budget could be divided over the subsystems and interfaces in the control loop.

In the present embodiment, possible latency sources here include but are not limited to the sensor 20, the controller 16, and the stimulation system 18, as well as one or more wireless or cable-bound connections between these modules.

Figure 8:
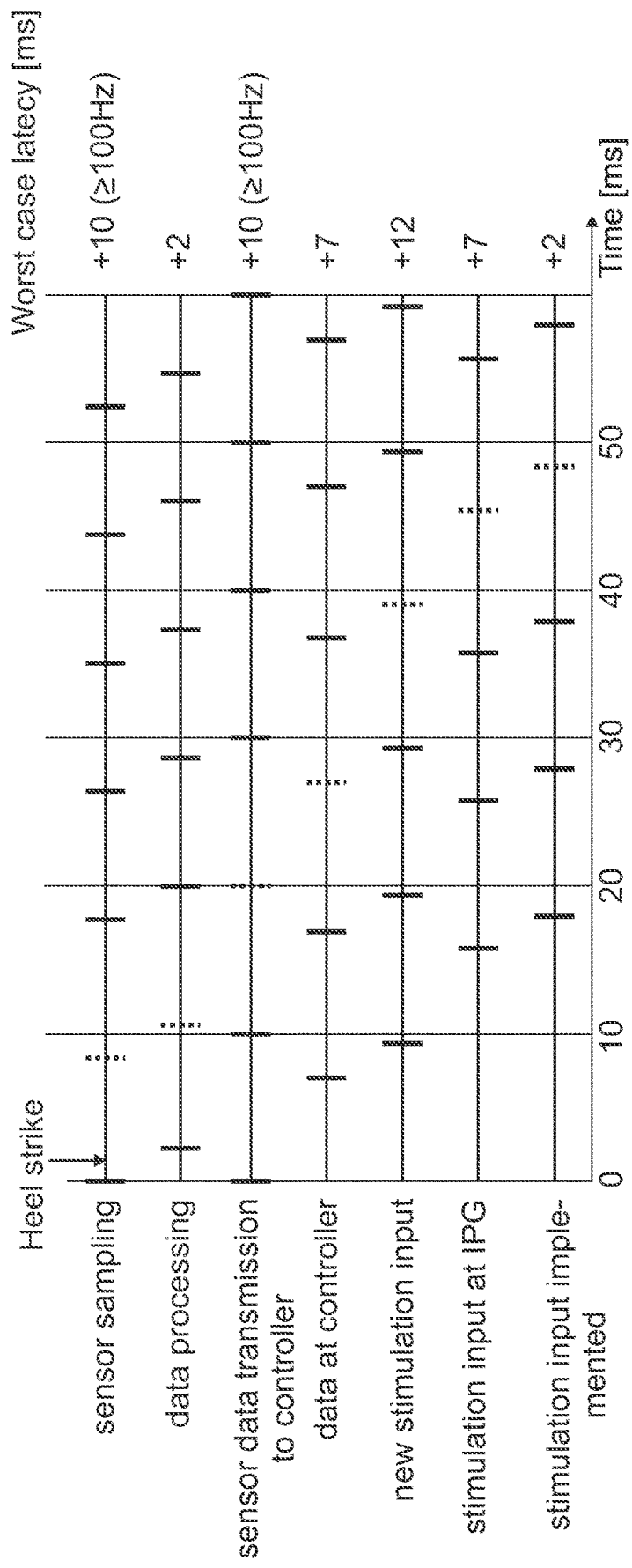
FIG. 8 the flow of information in the closed-loop system over time, and corresponding worst-case latencies.

In particular, the possible sources of latency include but are not limited to: sensor sampling, sensor data processing, sensor data transmission to the controller 16 (here via the sampling module 12), sensor data processing at the controller 16, generation of new stimulation input from by the controller 16, stimulation data transmission to the stimulation system 18, implementation of the stimulation input by the stimulation system 18, cf. FIG. 8.

However, additional subsystems (including but not limited to a controller, a pulse generator, a sensor network, a processor, a communication module and a telemetry module) may be also sources of latency.

To ensure that the total latency is kept within limits, the total allowed latency in the control loop (without latency compensation) may be set to a fixed time.

The allowed overall latency budget is here 100 ms.

In an alternative embodiment, the allowed overall latency budget could less then 100 ms.

In an alternative embodiment, the allowed overall latency budget could be 50 ms.

In another alternative embodiment, the allowed latency budget could also be less than 50 ms.

However, also every other allowed overall latency budget could generally be possible.

The controller 16 could have an allowed latency budget of approx. 10-15 ms, especially approx. 11-13 ms, preferably approx. 12 ms.

Similarly, the possible subsystem controller could have an allowed latency budget of approx. 10-14 ms, especially approx. 11-13 ms, preferably approx. 12 ms.

The subsystem sensor network could have an allowed latency budget of approx. 15-20 ms, especially approx. 16-18 ms, preferably approx. 17 ms.

The stimulation system could have an allowed latency budget of approx. 0.1-3.0 ms, especially approx. 1.5-2.5 ms, preferably approx. 2.0 ms.

Moreover, the telemetry module TEL may have an allowed latency budget of approx. 5-10 ms, especially approx. 6-8 ms and preferably approx. 7 ms, especially wherein out of the 7 ms a larger part of the latency budget may be for waiting time for establishing a telecommunication link and a smaller part of the latency budget may be a buffer to accommodate with the technological natural latency of the near field magnetic induction module (NFMI).

The pulse generator could have an allowed latency budget of approx. 0.1-3.0 ms, especially approx. 1.5-2.5 ms, preferably approx. 2.0 ms.

It is also not shown in FIG. 7 that remote control of the control system 10 could be generally possible.

It is also not shown in FIG. 7 that the control system 10 is a closed-loop system.

However, it could generally also be possible that the control system 10 is an open-loop system.

Not shown in FIG. 7 is that the control system 10 could comprise a pre-warning module, which is configured and arranged to provide a pre-warning signal indicative of providing an upcoming stimulation event.

In particular, the pre-warning signal may act in a sub-motor threshold region at which a sensation is evoked, but not a motor response.

FIG. 8 illustrates the flow of information in the closed-loop system of the control system 10 disclosed in FIG. 7 over time, and corresponding worst-case latencies.

In this embodiment, potential latency sources include but are not limited to: sensor sampling, sensor data processing, sensor data transmission to the controller 16 (here via the sampling module 12), sensor data processing at the controller 16, generation of new stimulation input from by the controller 16, stimulation data transmission to the stimulation system 18, here an IPG, implementation of the stimulation input by the stimulation system 18.

The flow of information over time (ms) is shown.

The dashed marks illustrate the information flow following a heel strike.

In this illustration, the motion data is sampled at 114 Hz and transmitted at the rate of 100 Hz to the controller 16.

However, also other sampling rates and transmission rates of motion data to the controller 16 are generally possible.

Figure 9:
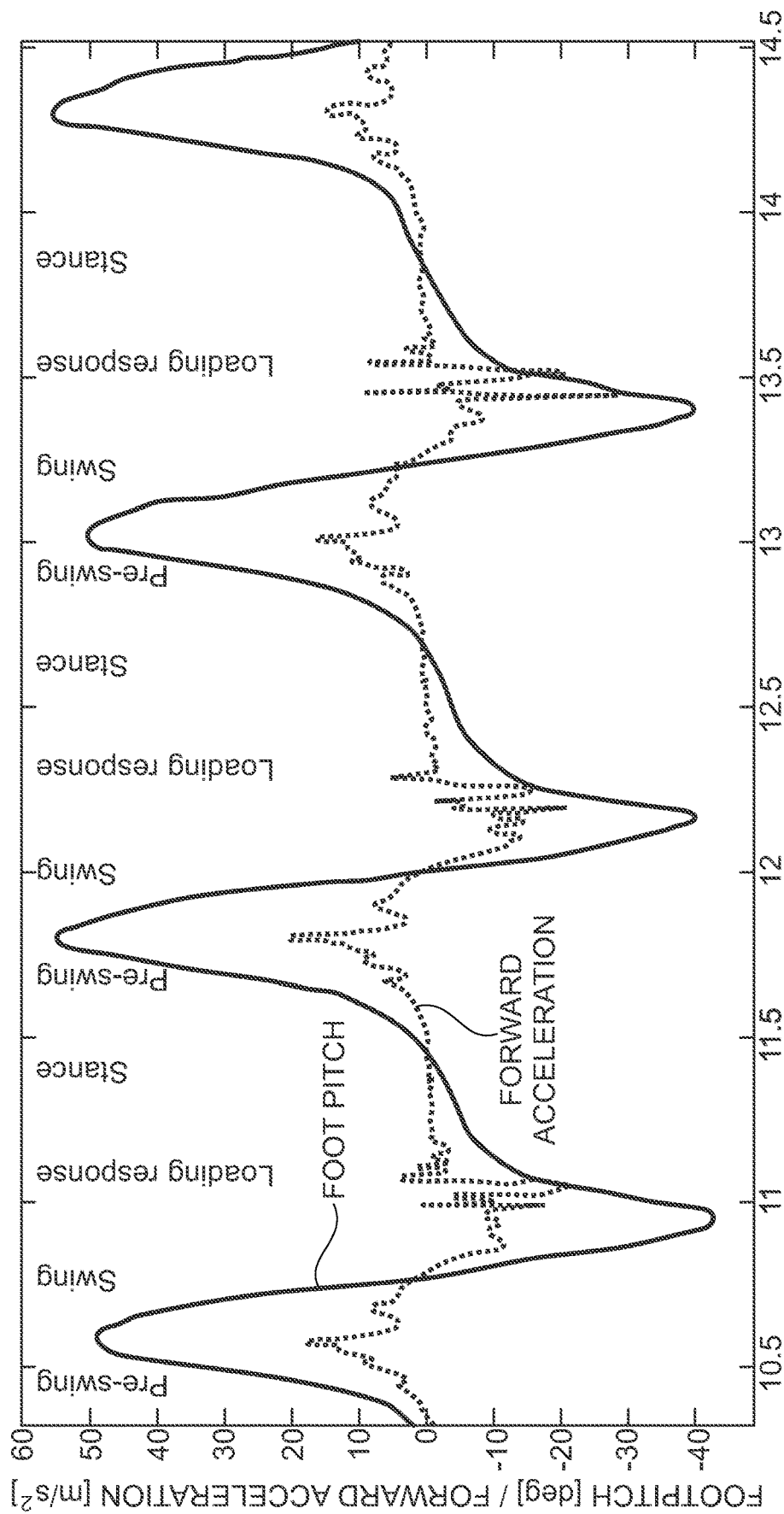
FIG. 9 a schematic diagram of foot pitch/forward acceleration of a patient.

FIG. 9 shows a schematical diagram of foot pitch/forward acceleration of a patient equipped with the control system disclosed in FIG. 7.

Here, a patient is equipped with one sensor 20 per foot.

In this embodiment, the sensor 20 is an IMU.

Alternatively, the patient could be equipped with the control system 10 described in FIG. 7 including one IMU and a shoe insole comprising a sensor network for the left or the right foot.

In another embodiment, the patient could be equipped with two or more IMUs per foot.

Further, the IMU and/or the shoe insole comprising the sensor network can be replaced by another type of sensor 20 including but not limited to e.g. a piezo element.

In this embodiment, it could be possible that the piezo element is integrated in wearables like e.g. a sock, a knee sock, tights, a shoe.

The foot pitch (degree) and forward acceleration (meter per $s^2$) of the right foot of a patient equipped with the control system 10 disclosed in FIG. 7 during walking is shown.

From these signals, clearly the cadence, pre-swing, swing, loading response and stance can be identified.

The same events and parameters can be identified for the left foot.

As walking is a periodic motion, all measured signals are also periodic.

Hence, it is always possible to estimate the cadence by extracting the base frequency of the measured signals.

By combining gait phase and cadence information of both feet of the patient together with the gait phase and cadence of the stimulation input, including the latency prediction, a reliable gait phase and cadence estimate can be provided.

Note that gait can vary a lot between different patients P as well as for a single patient for different walking speeds and different assistive devices (body-weight support, walker, crutches, etc.).

Especially for impaired gait, not all gait events are always present.

Moreover, machine-learning methods can be used to adapt the gait phase estimation to the specific gait of the patient.

The level of agreements and discrepancies between motion of the left and right foot, and the stimulation input, can be used to give an indication of the gait phase estimation reliability, e.g., the measured cadence of the left foot should be equal to the measured cadence of the right foot and the cadence of the provided stimulation, and the left foot and right foot should be (roughly) in anti-phase.

In the control loop also use can be made of the realization that the feet do not move independently from each other but are connected mechanically via the hip and on neural level via the spinal cord.

In particular, inhibitory reflex circuits in the spinal cord modulate neural firing rates (and hence modulate recruitment of motor neurons through EES).

Note that the example control and estimation routines included herein can be used with various system configurations. The control methods and routines disclosed herein may be stored as executable instructions in non-transitory memory and may be carried out by a control system 10 e.g. as a part of the controller 16 in combination with the sampling module 12, the prediction module 14, the stimulation system 18 and the subsystems sensor 20, controller, a pulse generator, a sensor network, a communication module COM, a telemetry module TEL, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the controller 16, where the described actions are carried out by executing the instructions in a control system 10 including the various hardware components.

REFERENCES 12 sampling module
14 prediction module
16 controller
18 stimulation system
20 sensor
CMB custom muscle block
COM communication module
EES epidural electrical stimulation
FES functional electrical stimulation
FMB functional muscle block
IPG implantable pulse generator
WSN wireless network, connection
TEL connection, telemetry line
LVLat left vastus lateralis
RVLat right vastus lateralis
LIl left iliopsoas
RIl right iliopsoas
LRF left rectus femoris
RRF right rectus femoris
LST left semitendinosus
RST right semitendinosus
LTA left tibialis anterior
RTA right tibialis anterior
LMG left medial gastrocnemius
RMG right medial gastrocnemius
LSol left soleus
RSol right soleus
LFHL left flexor halluces longus
RFHL right flexor halluces longus

The invention claimed is:

1. A control system for a movement reconstruction and/or restoration system for a patient, comprising
at least one sensor or sensor network configured to sample signals describing body motion at a sampling rate of at least 50 Hz;
wherein the sensor network is a wireless sensor network;
at least one stimulation system configured to provide stimulation for movement reconstruction and/or restoration to the patient;
a prediction module configured to provide a prediction of at least a next movement to reduce latency and to synchronize stimulation to the movement phase, wherein the control system further comprises at least one controller, the controller being configured to provide stimulation control signals to the stimulation system on the basis of the information obtained by the at least one sensor or sensor network and the prediction provided by the prediction module.

2. The control system according to claim 1, wherein the sampling rate is at least 75 Hz.

3. The control system of claim 1, wherein the control system is configured to allow an overall latency budget, the latency budget being distributed to one or more subsystems of the control system.

4. The control system of claim 3, wherein the allowed overall latency budget is 100 ms or less.

5. The control system of claim 3, wherein the subsystems include at least one of the at least one sensor or sensor network, a controller, a pulse generator, a programmer, a communication module (COM), a telemetry module (TEL).

6. The control system of claim 5, wherein the control system is configured and arranged such that the controller has an allowed latency budget between one of 10-15 ms or and 11-13 ms.

7. The control system of claim 5, wherein the telemetry module comprises a near field magnetic induction module (NFMI).

8. The control system of claim 7, wherein the control system is configured and arranged such that the telemetry module (TEL) has an allowed latency budget between 5-10 ms and wherein out of the latency budget, a larger part of the latency budget is for waiting time for establishing a telecommunication link and a smaller part of the latency budget is a buffer to accommodate with the technological natural latency of the near field magnetic induction module (NFMI).

9. The control system of claim 5, wherein the control system is configured and arranged such that the sensor network has an allowed latency budget of approx. 15-20 ms.

10. The control system of claim 5, wherein the control system is configured and arranged such that the pulse generator has an allowed latency budget of approx. 0.1-3.0 ms.

11. The control system of claim 5, wherein the control system is configured and arranged such that the controller has an allowed latency budget of approx. 10-14 ms.

12. The control system of claim 5, wherein the prediction module is connected directly and/or indirectly with the at least one sensor or the sensor network and wherein the prediction module is configured to predict patient motion and/or movement on the basis of sensor input data, or to manage and/or monitor latency of the control system in order to stay within an overall allowed latency budget.

13. The control system of claim 1, wherein the control system comprises a latency budget monitoring and/or management system, which is configured and arranged to monitor and manage the overall latency of the control system by monitoring and/or managing latency of subsystems of the control system.

14. The control system of claim 1, wherein the control system is a closed-loop system.

15. The control system of claim 1, wherein the control system has a pre-warning module, which is configured and arranged to provide a pre-warning signal indicative of providing an upcoming stimulation event.

16. A method for a control system, comprising:
responsive to detecting motion at least one sensor or sensor network configured to detect an indication of movement at a region of a patient;
wherein the sensor network is a wireless sensor network;
sampling data from the at least one sensor or sensor network at a sampling module at a threshold sampling rate;
predicting a motion at the region of the patient by a prediction module;
collecting the data from the at least one sensor or sensor network and the prediction module at a controller configured to process the data; and
stimulating movement at the region of the patient by generating a pulse signal via a stimulation system based on the processed data from the controller.

17. The method of claim 16, wherein detecting motion at the at least one sensor or sensor network includes receiving three-dimensional accelerations, angular velocities, and orientations from an inertial measurement unit and wherein the inertial measurement unit includes an accelerometer and a gyroscope.

18. The method of claim 16, wherein sampling data at the at least one sensor or sensor network includes obtaining data from the at least one sensor or sensor network at a minimum rate of 50 Hz.

19. The method of claim 16, wherein stimulating movement via the stimulation system includes electronically stimulating neurons by at least one of a central nervous system (CNS) stimulation system and a peripheral nervous system (PNS) stimulation system.

* * * * *

UNITED STATES PATENT AND TRADEMARK OFFICE
CERTIFICATE OF CORRECTION

PATENT NO. : 11,524,159 B2
APPLICATION NO. : 16/682873
DATED : December 13, 2022
INVENTOR(S) : Miroslav Caban et al.

It is certified that error appears in the above-identified patent and that said Letters Patent is hereby corrected as shown below:

In the Claims

Claim 6, Column 26, Lines 38-39, "one of 10-15 ms or and 11-13 ms" should read --one of 10-15 ms or 11-13 ms--.

Signed and Sealed this
Fourteenth Day of March, 2023

Katherine Kelly Vidal
*Director of the United States Patent and Trademark Office*